United States Patent [19]

Wang

[11] Patent Number: 4,649,559
[45] Date of Patent: Mar. 10, 1987

[54] DIGITAL RADIOGRAPHY DEVICE
[75] Inventor: Shih-Ping Wang, Los Altos, Calif.
[73] Assignee: Xonics Imaging, Inc., Sunnyvale, Calif.
[21] Appl. No.: 546,962
[22] Filed: Oct. 31, 1983
[51] Int. Cl.[4] .............................................. G03B 41/16
[52] U.S. Cl. ..................................... 378/146; 378/99
[58] Field of Search .................... 378/146, 99; 358/111
[56] References Cited
U.S. PATENT DOCUMENTS

| 4,179,100 | 12/1979 | Sashin | 378/146 |
|---|---|---|---|
| 4,383,327 | 5/1983 | Kruger | 378/146 |
| 4,404,591 | 9/1983 | Bonar | 378/146 |
| 4,504,859 | 3/1985 | Grady | 358/111 |

Primary Examiner—Craig E. Church
Assistant Examiner—John Freeman
Attorney, Agent, or Firm—Allegretti, Newitt, Witcoff & McAndrews, Ltd.

[57] ABSTRACT

A large area, digital radiography apparatus in which a prescatter and a postscatter collimator are moved simultaneously with an x-ray image intensifier tube whose output display is scanned by a stationary scanning camera to produce a digitized x-ray image over a large cross-sectional area of the patient.

3 Claims, 6 Drawing Figures

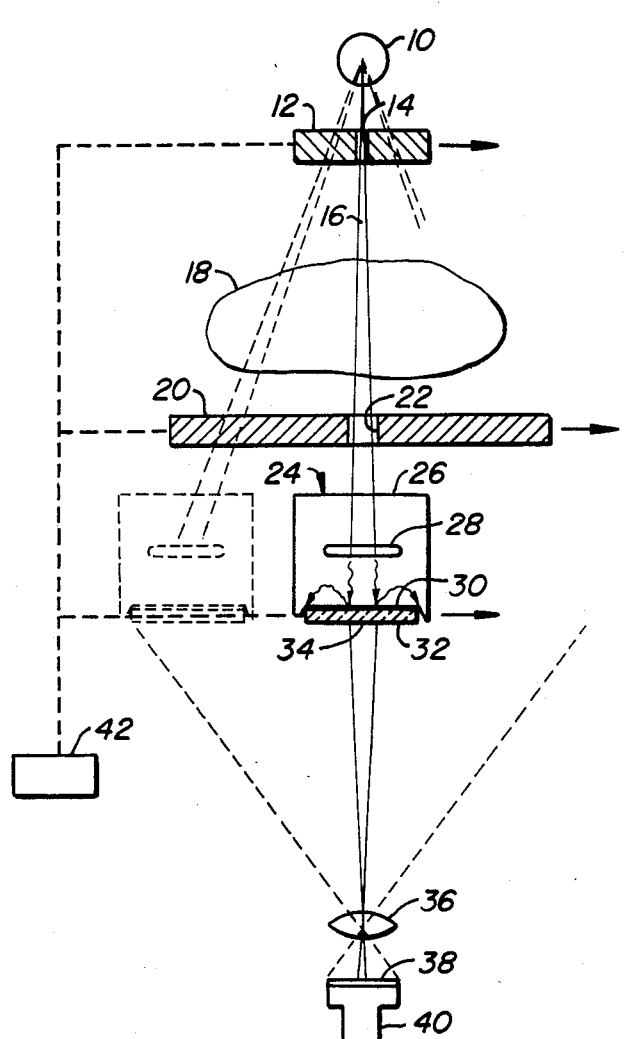
FIG._1.
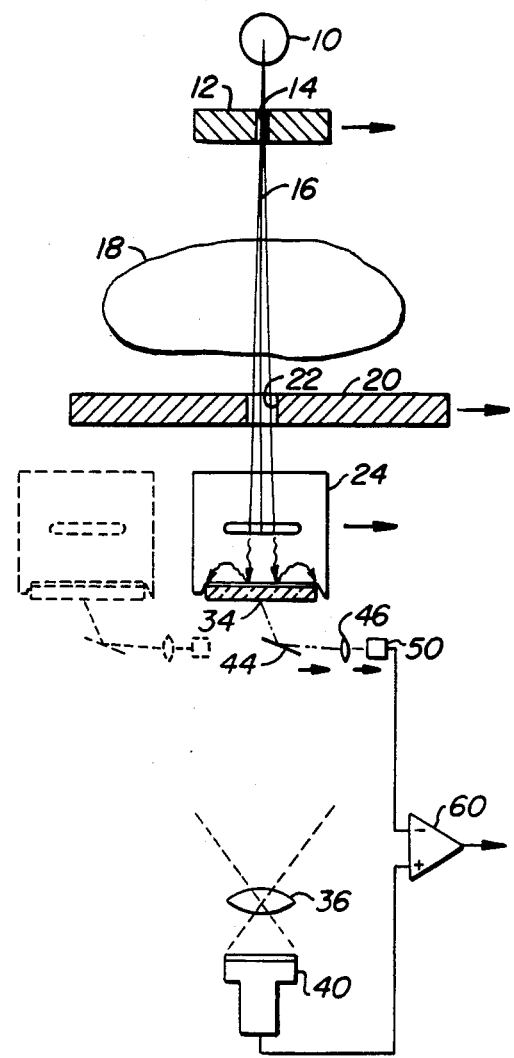
FIG._2.
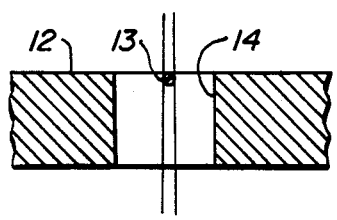
FIG._3.
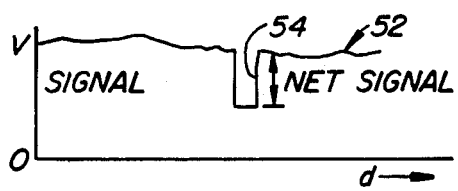
FIG._4.
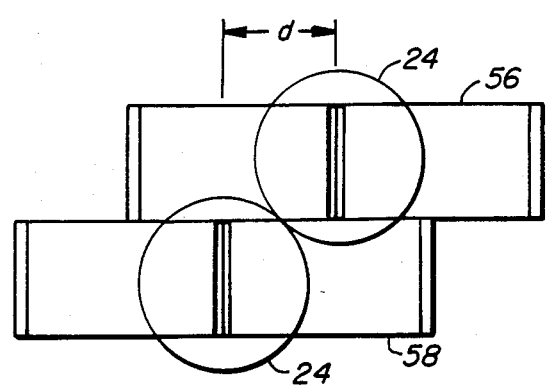
FIG._5.

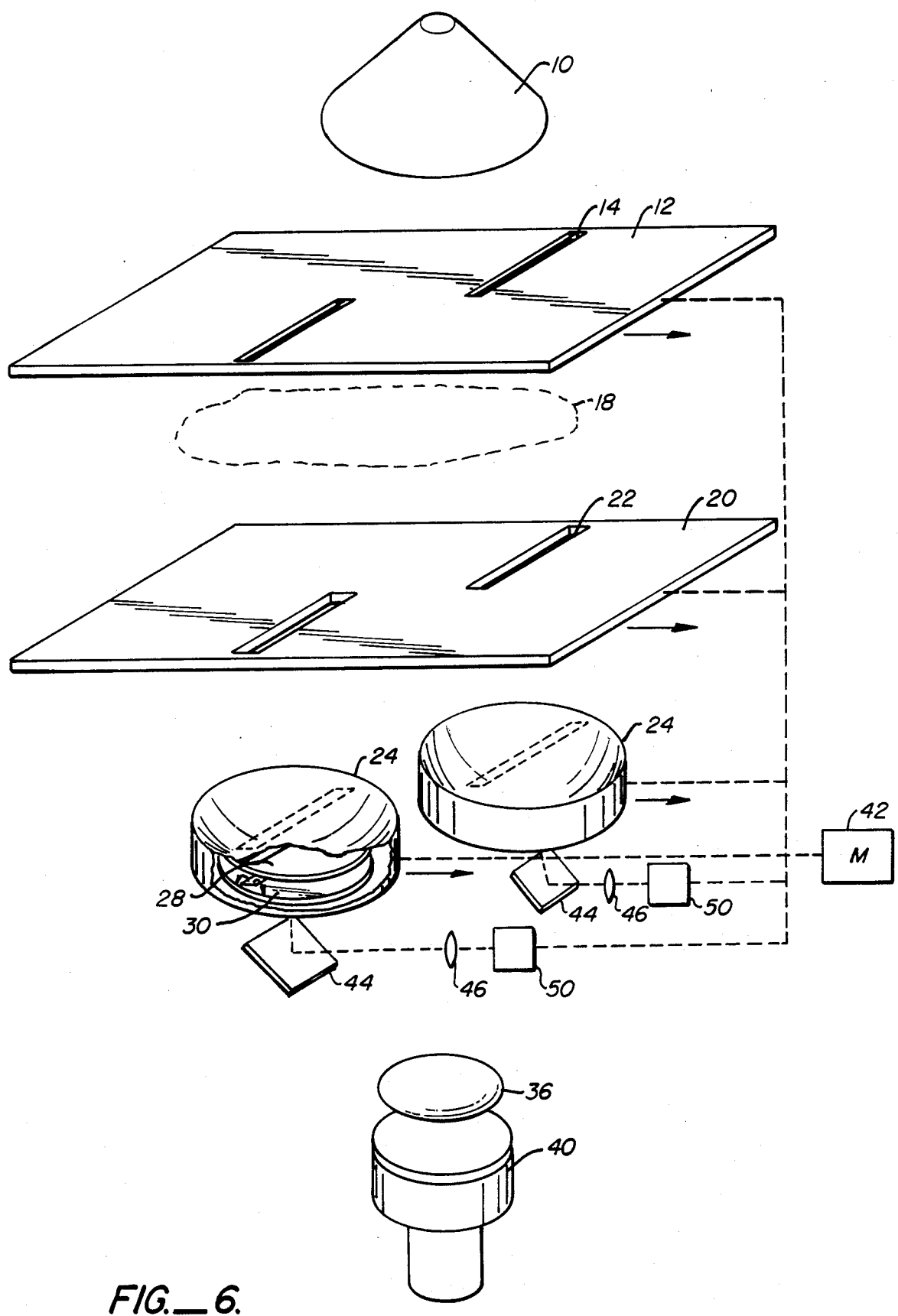
FIG._6.

DIGITAL RADIOGRAPHY DEVICE

1. Background Art

Various digital radiography systems have been proposed such as that by Sashin (U.S. Pat. No. 4,203,037) and the system described in the applicant's copending application Ser. No. 194,909, filed Oct. 7, 1980 and entitled X-Ray Intensifier Detector System for X-Ray Electronic Radiography. Both systems use prescatter and postscatter collimators which are simultaneously moved so as to produce a scanning, x-ray fan beam which sweeps through the patient and impinges upon an x-ray detector system.

One problem with the applicant's device, which employs an x-ray image intensifier tube as the detector, is in building an x-ray image intensifier tube of sufficient target area to intercept a wide fan beam as it is swept through the entire patient. Because such tubes are evacuated, certain constructional problems are encountered once a tube having a large crosssectional area is required.

2. Disclosure of Invention

The above and other problems of prior art digital radiography systems are overcome by the present invention of an apparatus for taking a radiograph of a patient which comprises a source of radiation, a movable prescatter collimator positioned between the radiation source and the patient, movable image display means located on the opposite side of the patient from the radiation source for displaying a radiographic image, and a movable postscatter collimator located between the patient and the image display means. Means are provided for simultaneously and synchronously moving the prescatter collimator, the postscatter collimator, and the image display means relative to the patient. Scanning means are employed for scanning the radiographic image presented by the display means and for converting said radiographic image into a corresponding output signal.

In the preferred embodiment, the image display means is one or more proximity type image intensifier tubes arranged side by side. The scanning means is one or more TV scanning cameras and suitable focusing lenses.

In a modified version of the invention, a radio-opaque wire is placed lengthwise in the slit of the prescatter collimator to cast a line shadow. The portion of the output display on which the shadow falls is, in turn, focused on a linear diode array. The signal derived from the output of the linear diode array can be taken as representational of the portion of the entire output signal due to scatter and/or flare. This signal can be used for generating a signal which is subtracted from the overall output signal to nullify the effects of scattered radiation and/or flare in the display means.

It is therefore an object of the present invention to provide a wide area digital radiography apparatus.

It is yet another object of the present invention to provide a large area, digital radiography device in which compensation is provided for flare and/or scatter.

The novel features which are believed to be characteristic of the invention, both as to organization and method of operation, together with further advantages thereof, will be better understood from the following drawings, in which several preferred embodiments of the invention are illustrated by way of example.

BRIEF DESCRIPTION OF DRAWINGS

FIG. 1 is a schematic illustration of a form of x-ray apparatus of the present invention;

FIG. 2 is a schematic illustration of a modification of the embodiment depicted in FIG. 1;

FIG. 3 is an enlarged, schematic illustration of the prescatter collimator of the embodiment depicted in FIG. 2;

FIG. 4 is a waveform diagram for use in explaining the operation of the apparatus depicted in FIG. 2;

FIG. 5 is a plan view of the x-ray detector arrangement of still another embodiment of the invention; and FIG. 6 is a schematic illustration of the embodiment depicted in part in FIG. 5.

BEST MODE FOR CARRYING OUT THE INVENTION

Referring now more particularly to FIG. 1, an x-ray tube source 10 generates a beam of x-rays which impinges upon a prescatter collimator 12 having a slit 14 therein. The portion of the x-ray beam emerging from the slit 14 has a fan shape 16 which passes through a stationary patient 18. The fan beam exiting from the patient impinges upon a postscatter collimator 20 having a slit 22 therein. The slits 14 and 22 are aligned with each other.

The fan beam image passing through the slit 22 strikes a proximity type image intensifier tube 24 having an input window 26 and an input screen 28 for converting the x-ray image into a pattern of photo-electrons which are then electrostatically accelerated toward the output phosphor display screen 30, deposited on the exit window 32. This will produce a light output line image 34 on the display screen 32. The image 34 is optically focused by a lens 36 onto the photosensitive target 38 of a TV scanning camera 40.

The prescatter collimator 12, postscatter collimator 20, and the proximity image intensifier tube 24 are all mechanically connected together to a motor drive unit 42 so that they can be moved synchronously in planes which are parallel to each other and which are perpendicular to the moving x-ray fan beam 16. The lens 36 is stationary and projects the image 34 onto the photosensitive target 38 so that the image scans across the face of the target in proportion to the movement of the x-ray image intensifier tube.

In some embodiments, the photosensitive target 38 can be of the persistent image type so that the entire x-ray image of a complete scan sweep can be recorded and then read off the target by the scanning mechanism of the TV camera, or alternatively, the TV camera can scan the image synchronously with the movement of the projected image on the TV tube so that the image is simultaneously scanned and digitized.

While in the preferred embodiment, the x-ray image intensifier tube moves in a plane, as described above, in other embodiments, the x-ray image intensifier tube could move along a curved surface so that the output image will also be on a curved surface to accommodate the focusing lens 36.

Referring now more particularly to FIG. 2, a modification of the apparatus depicted in FIG. 1 is illustrated. The modification consists of a tungsten wire 13 suspended lengthwise in the middle of the prescatter collimator slit 14 of the collimator 12. This is best illustrated in FIG. 3. The wire 13 casts a shadow in the x-ray beam 16 which shadow appears in the output display image 34 on the output screen of the image intensifier tube 24. The portion of the display image falling within this shadow is reflected by a traveling mirror 44 to a lens 46 which focuses the image onto a linear diode array 50. The array 50 is arranged to extend in the same direction as the shadow cast by the wire 13.

The mirror 44, the lens 46 and the array 50 are mechanically coupled to the proximity tube 24, the postscatter collimator and the prescatter collimator 12 so that they all move in synchronism. The mirror 44 is arranged out of the direct line of vision of the lens 36 so that it does not block the receipt of the image by the tube 40.

An output signal taken from the tube 40 presents a video signal waveform 52 similar to that illustrated in FIG. 4. A relatively high amplitude level signal will be produced by the scanning beam of the tube 40 up to the point where the shadow cast by the wire 13 is encountered. There the video output signal drops and produces a notch 54 in the waveform. After passing over the shadow, the signal resumes its former amplitude. Note that in the waveform 52 the depth of the notch 54 is not to a zero amplitude. This is because of flare in the output of the proximity tube 24 and patient x-ray scatter. The net signal which is desired to be obtained is that between the top and the bottom of the notch 54 in the waveform 52. Thus the output of the linear diode array 50 is used to generate a signal whose amplitude corresponds to the bottom of the notch 54. This signal is then subtracted in a differential amplifier 60 from the output signal 52 of the TV camera 42 to produce an output signal which is based on the true x-ray image. This signal can also be separately digitized, stored, and later subtracted from the digitized image by the TV camera in an image processor.

In FIG. 5 a pair of such x-ray image detectors is illustrated in plan view. Here, two proximity type image intensifier tubes 24 are movably mounted side-by-side to produce a pair of line images 34 which are off-set by a finite distance d in the direction of travel of the detector system as a whole. The areas covered by their scans are 56 and 58. Referring to FIG. 6, corresponding pairs of off-set, movable side-by-side prescatter and postscatter collimators, in the general arrangement of the embodiment depicted in FIG. 1, are mechanicaly linked to the motor drive unit 42.

It can be seen that by proper alignment of the tubes 24, the end of one line image 34 can be made to coincide with the beginning of the adjacent line image 34, but off-set from it by a distance d. This distance can be compensated for during video processing by conventional video graphic techniques to produce a single combined line image which covers twice the width of a single tube.

Furthermore, it can be seen that the field size of the x-ray field can be adjusted by simultaneously adjusting one or more of the system components; for example, the height of the collimators 12 and 20, the scan distance or scan angle as controlled by motor drive unit 42, the zoom setting of lens 36 and the location of TV camera 40. This ability to adjust x-ray field size is needed to provide the maximum system resolution and minimum x-ray dose to the body part to be radiographed.

The terms and expressions which have been employed here are used as terms of description and not of limitation and there is no intention, in the use of such terms and expressions, of excluding equivalents of the features shown and described, or portions thereof, it being recognized that various modifications are possible within the scope of the invention as claimed.

What is claimed is:

1. Apparatus for taking a radiograph of a stationary patient comprising a moving fan beam of x-rays defined by an x-ray source and a moving prescatter collimator slit located between the x-ray source and the stationary patient, at least one proximity type x-ray image intensifier device for the detection of the x-rays, said promimity type x-ray image intensifier device including an output screen for transforming the x-rays into a visible radiographic image, a post scatter collimator slit located between the patient and the proximity type x-ray image intensifier device, means for moving both collimator slits and the proximity type x-ray image intensifier device in unison, a stationary tv pick-up camera device with its lens focused at the plane of the output screen of the proximity type x-ray image intensifier device to pick-up the visible radiographic image and to transform said image into electric signals for further digital image processing.

2. Apparatus as recited in claim 1 wherein the proximity type x-ray image intensifier device comprises two or more proximity type x-ray image intensifier tubes.

3. Apparatus as recited in claim 1 wherein the moving fan beam of x-rays contains a lengthwise dark notch in the intensity of the x-rays caused by the blocking of the x-rays by a wire positioned lengthwise across the middle of the prescatter collimator slit, photooptical means for imaging the dark notch as it appears in the radiographic image of the proximity image intensifier device to produce an electrical output signal of the notch image, and means for removing the notch signal from the final radiographic image to produce an image with reduced scatter effects.

* * * * *